(12) United States Patent
Niklasson

(10) Patent No.: US 8,231,879 B2
(45) Date of Patent: Jul. 31, 2012

(54) TREATMENT OF DISEASES CAUSED BY VIRAL INFECTION

(76) Inventor: Bo Niklasson, Stockholm (SE)

( * ) Notice: Subject to any disclaimer, the term of this patent is extended or adjusted under 35 U.S.C. 154(b) by 0 days.

(21) Appl. No.: 12/143,904

(22) Filed: Jun. 23, 2008

(65) Prior Publication Data

US 2009/0004143 A1 Jan. 1, 2009

(51) Int. Cl.
*A61K 39/42* (2006.01)
*A61K 39/00* (2006.01)
*A61K 39/125* (2006.01)
*A61K 31/33* (2006.01)

(52) U.S. Cl. ............... 424/216.1; 514/183; 424/159.1; 424/178.1

(58) Field of Classification Search ............... None
See application file for complete search history.

(56) References Cited

U.S. PATENT DOCUMENTS

| | | | |
|---|---|---|---|
| 7,101,554 B2 * | 9/2006 | Niklasson | 424/186.1 |
| 7,442,380 B2 * | 10/2008 | Niklasson | 424/216.1 |
| 2004/0265793 A1 * | 12/2004 | Niklasson et al. | 435/5 |
| 2005/0233311 A1 * | 10/2005 | Lindberg et al. | 435/5 |

OTHER PUBLICATIONS

Wijesekera and Leigh, Amyotrophic lateral sclerosis, 2009, Orphanet Journal of Rare Diseases, vol. 4, No. 3, pp. 1-22.*
Niklasson et al., Could Myocarditis, Insulin-Dependent Diabetes Mellitus, and Guillain-Barre Syndrome Be Caused by One or More Infectious Agents Carried by Rodents?, 1998, Emerging Infectious Diseases, vol. 4, No. 2, pp. 187-193.*
Holmberg et al., Antiviral treatments reduce severity of diabetes in Ljungan virus-infected CD-1 mice and delay onset in diabetes-prone BB rats, 2009, Microbiology and Immunology, vol. 53, No. 10, abstract.*
Ansevin, Treatment of ALS With Pleconaril, Neurology, 2001, vol. 56, pp. 691-692, American Academy of Neurology.
Aberg et al., Impaired Glucose Tolerance During Pregnancy is Associated With Increased Fetal Mortality in Preceding Sibs, Acta Obstet Gynecol Scand, 1997, pp. 212-217, vol. 76.
Champsaur et al., Virologic, Immunologic, and Genetic Factors in Insulin-Dependent Diabetes Mellitus, The Journal of Pediatrics, 1982, pp. 15-20, vol. 100, No. 1, The C. V. Mosby Co.
Florea et al., Pleconaril, a Novel Antipicornaviral Agent, Pharmacotherapy, 2003, pp. 339-348, vol. 23.
Ginsberg-Fellner et al., Congenital Rubella Syndrome as a Model for Type 1 (insulin-dependent) Diabetes Mellitus: Increased Prevalence of Islet Cell Surface Antibodies, Diabetologia, 1984, vol. 27, pp. 87-89.
Girz et al., Sudden Fetal Death in Women With Well-Controlled, Intensively Monitored Gestational Diabetes, Journal of Perinatology, 1992, vol. XII, No. 3, pp. 229-233.
Hansson et al., Gradients in Density Variations of Small Rodents: The Importance of Latitude and Snow Cover, Oecologia, 1985, vol. 37, pp. 394-402, Springer-Verlag, Berlin.

Hansson et al., Rodent Dynamics As Community Processes, TREE, 1988, vol. 3, No. 8, pp. 195-200, Elsevier Publications, Cambridge.
Hornfeldt, Delayed ensity Dependence as a Determinant of Vole Cycles, Ecology, 1994, vol. 75, No. 3, pp. 791-806, Ecological Society of America.
Hornfeldt, Long-Term Decline in Numbers of Cyclic Voles in Boreal Sweden: Analysis and Presentation of Hypotheses, OIKOS, 2004, vol. 107, pp. 376-392.
Hughes, Phylogeny of the Picornaviridae and Differential Evolutionary Divergence of Picornavirus Proteins, Infection, Genetics and Evolution, 2004, vol. 4, pp. 143-152.
Lee et al., Isolation of the Etiologic Agent of Korean Hemorrhagic Fever, The Journal of Infections Diseases, 1978, vol. 137, No. 3, pp. 298-308.
Main et al., Characterization of Whitney's Clethrionomys Gapperi Virus Isolates From Massachusetts, Journal of Wildlife Diseases, 1976, vol. 12, pp. 154-164.
Murphy et al., Mortality and Morbidity Associated With Early-Onset Preeclampsia, Hypertension in Pregnancy, 2000, vol. 19(2), pp. 221-231, Marcel Dekker, Inc.
Nichol et al., Genetic Identification of a Hantavirus Associated With an Outbreak of Acute Respiratory Illness, Science, 1993, vol. 262, pp. 914-917.
Nicoletti et al., Correlation Between Islet Cell Antibodies and Anti-cytomegalovirus IgM and IgG Antibodies in Healthy First-Degree Relatives of Type 1 (Insulin-Dependent) Diabetic Patients, Clinical Immunology and Immunopathology, 1990, vol. 55, pp. 139-147, Academic Press, Inc.
Niklasson et al., Isolation of the Nephropathia Epidemica Agent in Sweden, The Lancet, 1984, pp. 1012-1013.
Nilsson, Slutenvardsregistrets Tillforlitlighet, Diagnosuppgifterna Battre An Sitt Rykte, Lakartidningen, 1994, vol. 91, pp. 602-605.
Notkins et al., Virus-Induced Diabetes Mellitus: Infection of Mice With Variants of Encephalomyocarditis Virus, Coxsackievirus B4, and Reovirus Type 3, 1977, pp. 137-145.
O'Sullivan, Diabetes Mellitus After GDM, Diabetes, 1991, vol. 29, Suppl. 2, pp. 131-135.

(Continued)

Primary Examiner — Benjamin P Blumel
(74) Attorney, Agent, or Firm — Kohn & Associates, PLLC

(57) ABSTRACT

A method of prophylactic and/or therapeutic treatment of a mammal for a disease that is caused by a Ljungan virus infection, such as Myocarditis, Cardiomyopathia, Guillain Barre Syndrome, and Diabetes Mellitus, Multiple Sclerosis, Chronic Fatigue Syndrome, Myasthenia Gravis, Amyotrophic Lateral Sclerosis, Dermatomyositis, Polymyositis, Spontaneous Abortion, Intrauterine Death, Preeclampsia, Sudden infant Death Syndrome, Bell's (facial) paralysis, Addison's disease, and Pernicious anemia, is described. An antiviral compound effective against a Ljungan virus, such as a compound effective against a picornavirus, e.g. Pleconaril or a derivative thereof, is used for the preparation of a medicament for the treatment of a disease in a mammal that is caused by a Ljungan virus infection, to eliminate or inhibit proliferation of the virus in the mammal and at the same time prevent and/or treat the disease in the mammal. A composition for treatment of a mammal for a disease caused by Ljungan virus infection including an antiviral compound, antiserum, and an interferon. A method of treatment of a mammal for a disease caused by a Ljungan virus infection.

7 Claims, 5 Drawing Sheets

OTHER PUBLICATIONS

Pevear, Activity of Pleconaril Against Enteroviruses, Antimicrobial Agents and Chemotherapy, 1999, vol. 43, No. 9, pp. 2109-2115, American Society for Microbiology.

Romero, Pleconaril: A Novel Antipicornaviral Drug, Expert Opinion on Investigation Drugs, 2001, vol. 10(2), pp. 370-379, Ashley Publications Ltd.

Sepa et al., Psychological Stress May Induce Diabetes-Related Autoimmunity in Infancy, Diabetes Care, 2005, vol. 28, No. 2, pp. 290-295.

Sonderegger-Iseli et al., Diagnostic Errors in Three Medical Eras: A Necropsy Study, The Lancet, 2000, vol. 355, pp. 2027-2031.

Suhonen et al., Hypertension and Pre-Eclampsia in Women With Gestational Glucose Intolerance, Acta Obstetrucua et Gynecologica Scandinavica, 1993, vol. 72, pp. 269-272, Denmark.

Vialettes et al., Stress Antecedents and Immune Status in Recently Diagnosed Type I (Insulindependent) Diabetes Mellitus, Diabete & Metabolisme, 1989, vol. 15, pp. 45-50, Paris.

Wales, Does Psychological Stress Cause Diabetes?, Diabetic Medicine, 1995, vol. 12, pp. 109-112, John Wiley & Sons, Ltd.

Webb et al., Susceptibility of Mice to Group B Coxsackie Virus is Influenced y the Diabetic Gene, The Journal of Experimental Medicine, 1976, vol. 143, pp. 1239-1248.

Whitney et al., Two Viruses Isolated From Rodents (*Clethrionomys gapperi* and *Microtus pennsylvanicus*) Trapped in St. Lawrence County, New York, Journal of Wildlife Diseases, 1970, vol. 6, pp. 48-55.

Williams, Pregnancy: A Stress Test for Life, Current Opinion in Obstetrics and Gynecology, 2003, vol. 15, pp. 465-471, Lippincott Williams & Wilkins.

Yoon et al., Isolation of a Virus From the Pancreas of a Child With Diabetic Ketoacidosis, Virus-Induced Diabetes Mellitus, 1979, vol. 300, No. 21, pp. 1173-1179.

Zhu et al., Statistical Analysis of Perinatal Outcomes in Pregnancy Complicated With Diabetes Mellitus, J. Obstet. Gynaecol. Res., 1997, vol. 23, No. 6, pp. 555-563.

Freimanis, T., et al., Effects of postnatal stress on the development of type 1 diabetes in bank voles (*Clethrionomys glareolus*), Int. J. Exp. Diabesity Res. 4(1):21-5 (2003).

Niklasson, B., et al., Isolation of the nephropathia epidemica agent in Sweden. Lancet, May 5; 1: 1012-3 (1984).

Johansson, S., et al., Molecular analysis of three Ljungan virus isolates reveals a new, close-to-root lineage of the Picornaviridae with a cluster of two unrelated 2A proteins, J. Virol. September; 76(17): 8920-30 (2002).

Niklasson, B., et al., Could myocarditis, insulin-dependent diabetes mellitus, and Guillain-Barre syndrome be caused by one or more infectious agents carried by rodents?, Emerging Infectious Diseases 4 (2):187-93 (1998).

Niklasson, B., et al., A new picornavirus isolated from bank voles (*Clethrionomys glareolus*), Virology 255(1):86-93 (1999).

Johansson, S., et al., Molecular analysis of three Ljungan virus isolates reveals a new, close-to-root lineage of the Picornaviridae with a cluster of two unrelated 2A proteins, J. Virol. 76 (17):8920-30 (2002).

Schoenecker, B., et al., Development of stereotypies and polydipsia in wild caught bank voles (*Clethrionomys glareolus*) and their laboratory-bred offspring. Is polydipsia a symptom of diabetes mellitus?, Applied Animal Behaviour Science 68 (4):349 (2000).

Niklasson, B., et al. Development of type 1 diabetes in wild bank voles associated with islet autoantibodies and the novel Ljungan virus, Int. J. Exp. Diabesity Res. 4 (1):35-44 (2003).

Niklasson, B., et al., Type 1 diabetes in Swedish bank voles (*Clethrionomys glareolus*): signs of disease in both colonized and wild cyclic populations at peak density. Ann. N Y. Acad. Sci. 1005:170-5 (2003).

* cited by examiner

TREATMENT OF DISEASES CAUSED BY VIRAL INFECTION

CROSS REFERENCE TO RELATED APPLICATIONS

The present application claims priority to International Patent Application PCT/SE04/000226 (International Publication Number WO 2004/073710), filed Feb. 19, 2004, which claims priority to U.S. Provisional Patent Application No. 60/448,452, filed Feb. 21, 2003 which is a continuation of U.S. Ser. No. 11/209,467, filed Aug. 22, 2005.

BACKGROUND OF THE INVENTION

1. Field of the Invention

The invention relates to the treatment of diseases caused by viral infection. More precisely, the invention relates to a method of prophylactic and/or therapeutic treatment of a mammal for a disease. The disease may be caused by viral infection in most tissues or cell types. For example, the disease may be in muscle tissues, neural cells, or endocrine glands caused by a Ljungan virus infection. The invention also relates to the use of an antiviral compound effective against a Ljungan virus for the preparation of a medicament for the treatment of a disease. The disease may be caused by viral infection in most tissues or cell types. For example, the disease may be in muscle tissues, neural cells, or endocrine glands caused by a Ljungan virus infection.

2. Background Art

Rodents are well-known reservoirs and vectors for viruses causing disease in humans. Puumala virus causing Nephropathia Epidemica (Myhrman, Nordisk Medicinsk Tidskrift, 7, 739-794, 1934; and Niklasson et al., Lancet, 1, 1012-3, 1984) is one example of an important human pathogen carried by bank voles. It has been demonstrated that the incidence rate of human Nephropathia Epidemica correlates with the vole population density during the previous year (Niklasson et al., Am. J. Trop. Med. Hyg., 53, 134-40, 1995). More recently, statistical evidence suggests that type 1 diabetes in humans also tracks the 3- to 4-year population density cycles of the bank vole with a similar time lag (Niklasson et al., Emerg. Infect. Dis., 4, 187-93, 1998). It was also observed that a high frequency of bank voles trapped in the wild and kept in the laboratory for studies of stereotypic behavior (Schoenecker et al., Appl. Anim. Behav. Sci., 68, 349-357, 2000) develop polydipsia and glucosuria at a high frequency.

Ljungan virus, belonging to the Picornavirus family, is carried by small rodents and causes diseases in other animals, including humans. The first three isolates were disclosed in the International Patent Application WO 98/11133 and the partial sequence of each was also comprised therein. The full sequences of these three Ljungan viruses have recently been published. (Johnsson S. et al., Journal of Virology, September 2002, p. 8920-8930)

Ljungan virus is a virus carried by small rodents. Ljungan virus belongs to the Picornavirus family. Ljungan virus is serologically and genetically distantly related to other members of the Picornavirus family. Ljungan virus will most likely form a new genus in the Picornavirus family.

Genetically, the Ljungan virus genome and the polyprotein encoded by them exhibit several exceptional features, such as the absence of a predicted maturation cleavage of VP0, a conserved sequence determinant in VP0 that is typically found in VP1 of other Picornaviruses, and a cluster of two unrelated 2A proteins. The 2A1 protein is related to the 2A protein of cardio, erbo and aphthoviruses and the 2A2 protein is related to the 2A protein of parechoviruses, kobuviruses and avian encephalomyelitis virus. (A. M. Lindberg and Susanna Johansson, Virus Research 85 (2002) 61-70).

Ljungan virus is characterized by a chronic or long lasting infection in its rodent host and reservoir. Ljungan virus can replicate and cause disease in a very broad host spectrum of animal species as well as in humans. Ljungan virus infects these different species of animals as well as humans and the infection does often result in a long lasting or chronic infection. Ljungan virus replicates in a wide variety of tissue culture cells giving a chronic infection with discrete CPE (cytopathogenic effect) and low viral output (in the order of 1000-100 000 viral particles per ml supernatant).

Data generated by virus cultivation under laboratory conditions show that Ljungan virus grows/replicates in a number of cell lines that originate from different tissues and different species, e.g. Vero monkey kidney; Vero E6 monkey kidney; MA-104 monkey kidney; CV-1 monkey kidney; GMK monkey kidney; A-549 human lung; Hela human cervical tissue; BHK 21 hamster kidney; RD human muscle; and L-cells mouse skin.

In living animals and humans Ljungan virus replicates in muscle tissue including heart tissue, in neural cell including the brain, in endocrine glands including the beta cells of the pancreas, the thyroid gland, the supra renal gland.

Data generated by detection of virus by Ljungan virus specific immunohistochemistry test, thin section electron microscopy and by PCR in humans, bank voles, lemmings, laboratory mice rabbits, guinea pigs, arctic foxes, and moose show that Ljungan virus has been found in endocrine and exocrine pancreas tissue, in endothelial cells of vessels, cells in the brain (including nerve tissue), cells of the liver, cells of the placenta and the umbilical cord, muscle tissue, heart tissue, tissue of the thyroid gland. The conclusion is that Ljungan virus can grow in most cell types of the body and therefore infect all organs of the body.

The only group of viruses that partly interferes with the above definition of Ljungan viruses are viruses in the cardio virus genus. There are some similarities among Ljungan viruses and viruses in the cardio virus genus. For example, cardioviruses belong to the picornavirus family, cardiovirus have rodents as their natural reservoir, cardioviruses can cause disease in a wide variety of animal species, and cardiovirus can infect and cause disease in the same organs as Ljungan virus. There are also some differences between Ljungan viruses and viruses in the cardiovirus genus. For example, cardiovirus and Ljungan virus are genetically distantly related, the double 2 A of Ljungan virus is absent in cardiovirus, cardiovirus is not related to Ljungan virus by serology, cardiovirus cause an acute disease (not long lasting or chronic) when it affects its non-rodent victims, cardiovirus is easy to cultivate in tissue culture without adaptation while Ljungan virus is often impossible to cultivate without blind passage in tissue culture or first passage in suckling mice and after several passages in suckling mice adaptation in tissue culture, and cardioviruses do not infect humans (only rare case reports in the literature).

New variants of Ljungan virus can be found in different continents. They will all be carried by small rodents and they will all cause the same disease syndromes in humans. The source for virus isolation/discovery can be selected/identified in different ways. For example, a wild rodent such as a mouse, rat or a vole with signs and symptoms similar to the diseases linked with Ljungan virus in humans (e.g. diabetes or myocarditis) can be found. Additionally, a screen of a large numbers of wild rodents by PCR using several different primer combinations targeting the conserved region of the Ljungan virus genome can be done. Further, a screen of a large number of wild rodents using specific antiserum can be performed. Antisera are collected from patients with the disease in humans linked with Ljungan virus that are living in the same geographic area as the rodents. Ljungan virus infected rodents are identified by immunostaining (e.g. immunohistochemistry) of formalin fixed organs. A portion of the same organ that is tested by immunohistochemistry is kept without fixation in a minus 70° C. freezer. The unfixed material is used for virus isolation if the immunohistochemistry turns out to be positive.

Tissue, from which virus isolation attempt will be made, is grinded and diluted in sterile saline or PBS. One-day old suckling mice are injected with 2-4 microliters of the tissue suspension intracerebrally. When suckling mice are used for virus isolation, in general all the mice die within a week of inoculation if a virus is present. However, Ljungan virus is different in that you have to wait 10 days to 3 weeks before signs of symptoms in the baby mice develop. Signs and symptoms are very discrete such as slow weight increase and altered mobility. Only 5-10% of the animals develop symptoms. This is very unusual and would in most cases result in a negative interpretation of the isolation attempt. Only the brain tissue from suckling mice with signs and symptoms are used for passage in new one-day old suckling mice.

When passed, the brains from sick suckling mice are grinded and diluted in sterile saline or PBS. One-day old suckling mice are injected with 2-4 microliters of the tissue suspension intracerebrally. Several such passages may be necessary before disease develops earlier (8-12 days) and in the majority of mice. After several passages in suckling mice Ljungan virus is inoculated into tissue culture such as Vero cells for amplification and identification.

Ljungan virus must be adapted to cell culture by passages of the cells. No or very discrete cytopathogenic effect is seen. The cells (not the tissue culture fluid) are passed weekly into new tissue culture bottles at a rate of 1 to 5. After 3-6 such blind passages the cells are stained using antibodies directed to the isolate. These antisera can be made by immunising adult mice with the suckling mouse brain suspension of a suspected isolate and/or by using human serum from patients with the disease caused by Ljungan virus living in the same geographic region as the animals used as source for virus isolation.

The ability to identify and associate an infectious agent with human disease is profoundly influenced by its biological characteristics. Infectious agents that are difficult to detect and cultivate increase the difficulties of linking the agent to disease. Additionally, zoonotic agents have low selective pressure for efficient growth in a human host, which can result in low pathogen concentrations, making viral identification difficult. Epidemiological observations on the vector often precede development of the diagnostic tools necessary for linking the agent to disease. In addition, incubation timer disease incidence and disease severity all influence the success of connecting a potential pathogen to human disease.

Hantavirus, which is a widely distributed viral infection with various rodent species serving as vectors, is a good example of the challenges involved in viral identification. In the human host, hantavirus manifests a range of within and between strain symptoms. Despite scientific attention drawn to the hemorrhagic fever characteristic of Old World hantavirus infection throughout much of the $20^{th}$ century, and the fact that incubation time is short and the disease severe or lethal, it was only in 1978 for Asia and in 1984 for Europe that the viral agents were identified, and in 1993 that the New World clade of this pathogen recognized. The discovery of hantavirus illustrates the need to integrate epidemiology, vector biology and microbiology to identify the cause of such zoonotic disease.

It was recently proposed that lethal myocarditis and type 1 diabetes (T1D) in humans can be caused by one or more infectious agents carried by rodents, based on the association between rodent density and disease incidence. Based upon these observations, a search for an etiologic agent in small rodents was done. This resulted in the isolation of a novel picornavirus from the most prevalent mammal in northern Europe, the bank vole (*Clethrionomys glareolus*). This virus is called the "Ljungan virus" after the Valley in Västernorrland County in Sweden where it was first observed.

The first observation of LV-related diseases was recently made in bank voles, which showed that animals in captivity developed diabetes. Polyuria, polydipsia, glucosuria, elevated blood glucose levels, ketoacidosis and deaths were observed. Lysis of pancreatic islet beta cells and presence of GAD65-, IA-2 and insulin auto-antibodies suggested that the bank voles suffered from a T1D condition. Bank voles colonized for more than a decade were studied in more detail and it was found that approximately 20% of the animals developed an abnormal glucose tolerance test, accompanied by high serum insulin levels, increased insulin release from isolated islets, and a glucose oxidation rate consistent with type 2 diabetes (T2D) (Blixt, M., Niklasson, B. & Sandier, S. Characterization of β-cell function of pancreatic islets isolated from bank voles developing glucose intolerance/diabetes: an animal model showing features of both type 1 and type 2 diabetes mellitus). Moreover, total destruction of beta cells was also found in these colonized bank voles, similar to the pathology observed in recently trapped voles from cyclic populations in northern Sweden. These animals thus go through a T2D-like phase with viable beta cells, evidence of insulin resistance indicated by abnormal glucose tolerance tests and high serum insulin levels with progression to T1D with total destruction of beta cells.

It has been recently found that a high proportion of live-trapped bank voles, grey sided voles (*C. rufocanus*), field voles (*Microtus agrestis*) and Norwegian lemmings (*Lemmus lemmus*) suffer from diabetes and myocarditis when tested at peak densities in cyclic populations in northern Scandinavia (Niklasson B, Nyholm E, Feinstein R E, Samsioe S, Lernmark Å, Hörnfeldt B. Virus-induced diabetes and myocarditis in voles and lemmings at cyclic peak densities). These diseases have been associated with LV infection in wild rodents, and compelling evidence suggests that infected animals develop disease when subjected to stress. LV-infected laboratory mice infected during the first weeks of life develop encephalitis, myocarditis and pancreatitis, followed by diabetes, as measured by abnormal glucose tolerance test 10-15 weeks after infection (Niklasson B, Nyholm E, Feinstein R E, Samsioe S, Lernmark Å, Hörnfeldt B. Virus-induced diabetes and myocarditis in voles and lemmings at cyclic peak densities). By inducing these diseases under controlled laboratory conditions Koch's postulates proving causality were fulfilled. The frequency of diabetes varied from approximately 80% of the male mice infected during the first three days of life to 30% of the male mice infected during the second week of life. Very few female mice developed diabetes.

SUMMARY OF THE INVENTION

The present invention provides a method of prophylactic and/or therapeutic treatment of a mammal for a disease that is caused by a Ljungan virus infection, such as Myocarditis, Cardiomyopathia, Guillain Barre Syndrome, and Diabetes Mellitus, Multiple Sclerosis, Chronic Fatigue Syndrome, Myasthenia Gravis, Amyotrophic Lateral Sclerosis, Dermatomyositis, Polymyositis, Spontaneous Abortion, Intrauterine Death, Preeclampsia, Sudden Infant Death Syndrome, Bell's (facial) paralysis, Addison's disease, and Pernicious anemia. Further, the present invention provides an antiviral compound effective against a Ljungan virus, such as a compound effective against a picornavirus, e.g. Pleconaril or a derivative thereof. The present invention also provides a preparation of a medicament for the treatment of a disease in a mammal that is caused by a Ljungan virus infection, to eliminate or inhibit proliferation of the virus in the mammal and at the same time prevent and/or treat the disease in the mammal. The present invention also provides a composition for treatment of a mammal for a disease caused by Ljungan virus infection including an antiviral compound, antiserum, and an interferon. Finally, the present invention provides a method of treatment of a mammal for a disease caused by a Ljungan virus infection.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
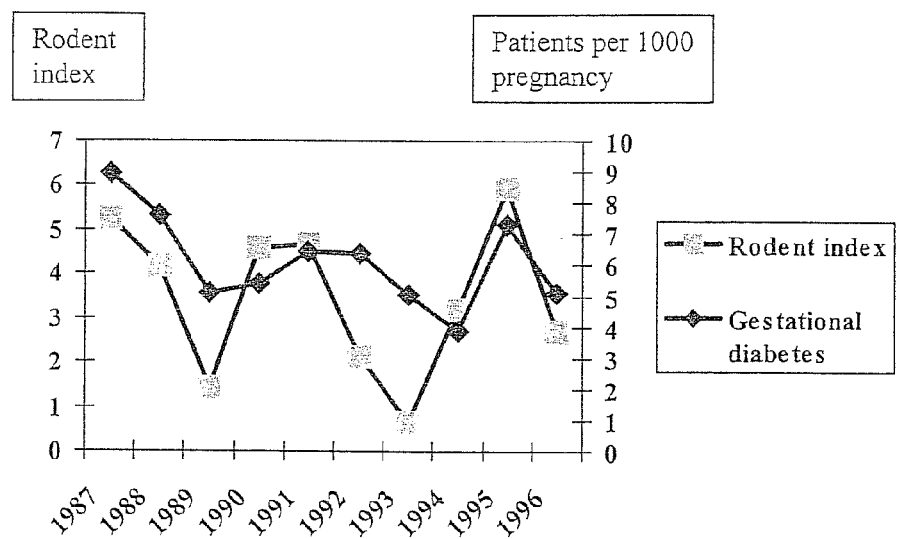
FIG. 1A-1C. The incidence of gestational diabetes, intrauterine fetal deaths and severe preeclampsia in two counties in northern Sweden during the autumn (July-December) of 1987-1996 compared to cyclic small rodent autumn trap index in the same region. Simple linear regression analysis, with the explanatory variable being the rodent index, proved significant for IUFD in FIG. 1B (p=0.000, coefficient of determination $R^2$=82%) and severe preeclamapsia (p=0.004, coefficient of determination $R^2$=66.7%) while gestational diabetes was not significant in FIG. 1A (p=0.110, coefficient of determination $R^2$=28.8%). No significant autocorrelation in the residuals were present. Details of materials and methods are available online.

The present invention is directed to a method of prophylactic and/or therapeutic treatment of a mammal for a disease that is caused by a Ljungan virus infection, comprising administration to said mammal of an antivirally effective amount of an antiviral compound effective against the Ljungan virus to eliminate or inhibit proliferation of said virus in said mammal and at the same time prevent and/or treat said disease in said mammal.

Preferably the mammal is selected from the group consisting of humans, horses, cattle, pigs, cats, dogs and rodents such as rats and mice.

The disease caused by Ljungan virus infection may be caused by the infection of a tissue or cell type. As indicated above, it is known that Ljungan virus is capable of growth in most cell types of the body and can therefore infect all organs of the body.

In a preferred embodiment of the invention the Ljungan virus infection is in at least one of muscle tissues, neural cells and endocrine glands of the mammal and the infection may also be in an organ, such as the liver.

In another embodiment the muscle tissue is heart tissue, the neural cells are brain cells, the endocrine glands are beta cells of pancreas, thyroid gland and/or supra renal gland.

In yet another embodiment the disease is selected from the group consisting of Myocarditis, Cardiomyopathia, Guillain Barre Syndrome, and Diabetes Mellitus, Multiple Sclerosis, Chronic Fatigue Syndrome, Myasthenia Gravis, Amyotrophic Lateral Sclerosis, Dermatomyositis, Polymyositis, Spontaneous Abortion, Intrauterine Death, Preeclampsia, Sudden Infant Death Syndrome, Intrauterine fetal death, Bell's (facial) paralysis, Addison's disease, and Pernicious anemia.

Preferably the antiviral compound is selected from compounds effective against a picornavirus.

All antiviral compounds effective against a picornavirus are at least partly also effective against Ljungan virus infection and are thus at least to some extent useful in the present invention.

At present the most preferred compound is Pleconaril or a derivative thereof.

Pleconaril: (3-[3,5-dimethyl-4-[[3-(3-methyl-5-isoxazolyl)propyl]oxy]phenyl]-5-(trifluoromethyl)-1,2,4-oxadiazole) (ViroPharma Inc., Picovir®).

The structural formula of Pleconaril is:

Compounds comprising Pleconaril and derivatives thereof are shown in U.S. Pat. No. 5,464,848, the European equivalent EP 0566199, and are claimed to have effect on picornaviral infections.

Other derivatives of Pleconaril claimed to have antiviral effects against picornavirus are disclosed e.g. in U.S. Pat. No. 4,945,164.

There are numerous antiviral compounds effective against picornaviruses disclosed in the prior art with several different modes of actions. Such compounds are for example Compounds that inhibit the proteolytic activity of picornaviral proteases disclosed in the patent application WO 9222570;

2-(4-pyridylaminomethyl)benzimidazole derivatives with in vitro and in vivo antipicornavirus activities disclosed in EP 0252507 B1.

Benzisoxazole derivatives for treatment of picornavirus infection disclosed in WO 0250045.

All the mentioned references are incorporated herein by reference.

Candidate compounds can be tested by use of animal models or in vitro infected cell or tissue cultures in a way known to a man skilled in the art, e.g as shown in the Examples below.

Another aspect of the invention is directed to the use of an antiviral compound effective against a Ljungan virus for the preparation of a medicament for the treatment of a disease in a mammal that is caused by a Ljungan virus infection.

Preferably the mammal is selected from the group consisting of humans, horses, cattle, pigs, cats, dogs and rodents such as rats and mice.

The disease caused by Ljungan virus infection may be caused by the infection of any tissue or cell type. As indicated above, it is known that Ljungan virus is capable of growth in most cell types of the body and can therefore infect all organs of the body.

In a preferred embodiment of the invention the Ljungan virus infection is in at least one of muscle tissues, neural cells and endocrine glands of the mammal, but the infection may also be in an organ, such as the liver.

In an other embodiment of this aspect of the invention the muscle tissue is heart tissue, the neural cells are brain cells, the endocrine glands are beta cells of pancreas, thyroid gland and/or supra renal gland.

In yet another embodiment the disease is selected from the group consisting of Myocarditis, Cardiomyopathia, Guillain Barre Syndrome, and Diabetes Mellitus, Multiple Sclerosis, Chronic Fatigue Syndrome, Myasthenia Gravis, Amyotrophic Lateral Sclerosis, Dermatomyositis, Polymyositis, Spontaneous Abortion, Intrauterine Death, Preeclampsia, Sudden Infant Death Syndrome, Intrauterine fetal death, Bell's (facial) paralysis, Addison's disease, and Pernicious anemia. In a preferred embodiment the antiviral compound is selected from compounds effective against a picornavirus. In a presently preferred embodiment the antiviral compound is Pleconaril or a derivative thereof.

In a further embodiment of the present invention, there is provided an anti-viral therapy that reduces the frequency of diabetes in Ljungan virus infected subjects. Ljungan virus-caused reproductive diseases are shown to be stress dependent in laboratory mice. In humans, the three diseases are associated with the population density of wild rodents and through relative levels of disease concurrence to each other. Immunohistochemistry, RT-PCR and serological tests document the presence of Ljungan virus in human disease. Case control studies of diabetes and preeclampsia show significant association of Ljungan virus with disease. As set forth in the examples below, epidemiological and experimental laboratory evidence indicates that a significant proportion of human diabetes, intrauterine fetal death and preeclampsia can be caused by Ljungan virus. This is supported by the fact that Ljungan virus causes diabetes and other diseases in both wild rodents and laboratory mice, in which the signs of both type 1 and type 2 diabetes can be present.

Another embodiment of the present invention is directed towards a composition for the treatment of diseases caused by viral infection, wherein the composition includes an antiviral compound, an antiserum, and an interferon. Preferably, the antiviral compound is Pleconaril, while the interferon is interferon α.

Medicament

While it is possible that an antiviral compound may be administered as the neat chemical, it is preferable to present the active ingredient as a pharmaceutical formulation or as a medicament.

A suitable medicament or pharmaceutical formulation useful in the present invention comprises an antiviral compound together with one or more pharmaceutically acceptable carriers and, optionally, other therapeutic and/or prophylactic ingredients. The carrier (s) must be acceptable in the sense that it should be compatible with the other active or inactive ingredients of the formulation and not deleterious to the recipient thereof.

The antiviral compounds used in the invention may also be used in combination with other anti-viral agents or other pharmaceuticals used in the treatment of viral infections.

Representative examples of other active ingredients include immunomodulators, immunostimulants, such as various interleukins, cytokines and antibody preparations, antibiotics and anti-inflammatory agents.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

Therapy

Antiviral Compound

An antiviral compound effective against Ljungan virus is in many cases the only active ingredient needed for termination of Ljungan virus infection and thereby reverse the disease in muscle tissues, neural cells, or endocrine glands that is caused by a Ljungan virus infection.

Interferon

The Ljungan virus is interferon sensitive. Interferon can have an effect if given before the infection or very early in the course of infection. Interferon is a class of soluble small proteins that inhibit virus multiplication. They are produced by cells infected by almost any animal virus (DNA or RNA). Preferably, the interferon is interferon α, but any interferon known to those of skill in the art can be utilized. Interferon can be used in combination with other therapeutic measures to terminate a chronic infection. The combination can be immunoglobulins, vaccination and antiviral compounds. This can be evaluated in an animal model.

Antibody

Data from picornavirus infection suggests that specific antibodies can be used in the treatment of severe and chronic infections. It can be used by it self or in combination with other therapeutic measures. Antibodies to Ljungan virus can be as polyclonal antibodies prepared from immune humans or animals or as human monoclonal antibodies or as "humanized" monoclonal antibodies originating from an animal system such as mice. The antibodies can be contained within a serum to form an antiserum or antisera used with the present invention. As is well known to those of skill in the art, antiserum is serum that includes an antibody or antibodies. The antiserum can be obtained from an animal that has been immunized either by injection of antigen into the body or by infection with microorganisms containing the antigen. Antisera can be monovalent (specific for one antigen) or polyvalent (specific for more than one antigen). The Ljungan virus antibodies can be used in combination with antiviral compounds and interferon to effectively treat diseases caused by Ljungan virus infection.

Determination of Presence of Ljungan Virus

The presence of Ljungan virus can be determined using any standard procedure including immunohistochemistry using antibody molecules having affinity for Ljungan virus or by using a labeled nucleic acid probe capable of specifically hybridizing to Ljungan virus nucleic acid. Alternatively the presence of Ljungan virus can be determined by detecting the presence of anti-Ljungan virus antibodies using a suitable test. Suitable techniques for determining the presence of Ljungan virus or anti-Ljungan virus antibodies are described in the examples below. Determination of the presence of Ljungan virus RNA by Polymerase Chain Reaction (PCR) is also described in the examples below.

EXAMPLES

Material and Methods
Reagents and Assays.

The brain from suckling mice infected intra-cerebrally at day 1 with the LV strains 145SL, 87-012 and 174F were used for immunization and infection. Antiserum to Ljungan virus was made by infecting/immunizing adult mice with a 10% suckling mouse brain homogenate (5). The immune sera were collected from the adult mice 6-8 weeks after infection. Mouse antiserum to the three different isolates were used separately for the immunohistochemistry test and pooled when used as therapy.

Pleconaril (VP-63843) a novel, orally bio-available, broad spectrum anti-picorna-viral agent developed as a therapeutic tool in entero- and rhino virus infections was also used alone or in combination with specific antiserum for intervention.

Glucose tolerance test was performed to determine the diagnosis of diabetes. In this test 2 g glucose per kg body weight was administrated intraperitoneally (as 100 mg glucose/ml solution). Blood glucose was measured (Medisence Precision PCx Abbott Laboratories) just before the glucose injection and at 60 and 120 minutes post administration. Diabetes was defined as a blood glucose level above 200 mg/dL in a glucose tolerance test at 120 min.

Abdominal fat in male mice was measured by dissecting out the bilateral scrotal fat cushion. The total weight of both fat cushions was used.

The serum insulin level was measured using a rat insulin high range ELISA kit (Mercodia AB, Uppsala, Sweden) according to the instructions of the manufacturer. Islets prepared from the pancreas were assayed for insulin release and glucose oxidation assay described elsewhere (Blixt, M., Niklasson, B. & Sandler, S. Characterization of β-cell function of pancreatic islets isolated from bank voles developing glucose intolerance/diabetes: an animal model showing features of both type 1 and type 2 diabetes mellitus. Manuscript submitted).

A real time RT-PCR was carried out in a 96-well microtiter plate format using consensus primers for the 5'end non-translated region of the genome (Donoso-Mantke O, Niklasson B, Kallies R, Nitsche A Meyer R and Niedrig M. First quantitative real-time reverse transcriptase PCR assay for detection of Ljungan virus manuscript submitted). This assay has been extensively evaluated using different culture and tissue specimens and proved to have a sensitivity of 10 RNA copies of all known strains of LV.

Immunohistochemistry staining was carried out on tissues fixed in 4% paraformaldehyde and embedded in paraffin. Briefly, the binding of mouse Ljungan virus antisera (diluted 1:3000 or more) to tissue was revealed by successive incubations with biotinylated anti-IgG, Vectastain peroxidase streptavidin ABC reagent (Vector Laboratories) and Vector Red substrate. Finally, slides were counter stained with methyl green, dehydrated, and mounted. High titer mouse antisera against two distinct Ljungan virus isolates, 87-012 and 145SL were used. Similarly produced antisera against members of other virus families such as Bunyavirus (Rift Valley Fever) and Togavirus (Ockelbo/Sindbis) and Flavivirus (Langat) as well as normal mouse serum were used. The specificity of the reaction was also evaluated by receiving a significant difference in signal/titer when testing after absorption with tissue culture grown LV antigen and control antigen.

Ljungan Virus in Laboratory Mice

Pregnant outbred CD1 mice (CD-1 (ICR) Br Charles River laboratories, Germany) were infected intraperitoneally with 1000 $ID_{50}$ units of LV145 SL two days after conception. Control animals were given an injection with the same volume with normal saline at the same time. All female mice were kept in individual cages and followed for the development of gestational diabetes, pregnancy outcome and development of diabetes in the offspring. In half of the infected pregnant mice, mild stress was induced by adding glucose (100 g/liter) to drinking water, performing weekly weights and glucose tolerance testing during the last week of pregnancy. The uninfected control group of pregnant mice was also subjected to stress. Antiviral therapy using LV-specific murine antisera or the oral antiviral compound Pleconaril (200 mg per kg body weight) administrated once a day for 4 consecutive days or a combination of antiserum and Pleconaril was initiated at 5 weeks of age (11-13). At 15 weeks animals were tested by a glucose tolerance test (GTT). Also, serum insulin level and abdominal fat were measured and the histopathology of the pancreas was examined.

The viral titer in different organs was measured by a real time RT-PCR in mice infected intreperitoneally at births. One group of six mice were sacrificed after one week with symptoms of severe encephalitis and another group of six mice surviving the acute encephalitis were sacrificed at 15 weeks of age.

Disease Incidence in Humans and Rodent Density

It has been suggested that gestational diabetes is associated with diabetes later in life (14). Gestational diabetes has also been associated with preeclampsia and IUFD (15). Based on these observations and work on LV in rodents, the temporal associations between the population density of wild voles and gestational diabetes, severe preeclampsia and intrauterine fetal deaths (IUFD) was investigated. The abundance of voles and other small rodents harbouring a virus that causes disease not only in rodents but also in humans might be reflected in the incidence of human morbidity. In southernmost Sweden, small rodent populations are non-cyclic, whereas rodent population abundance in the north fluctuates on a three- to four-year cycle. In Sweden long-term data on rodent abundance are available through the ongoing National Environmental Monitoring Programme from the northern, cyclic region but not from the southernmost non-cyclic region. Data from Vindeln, Västerbotten, in the north of Sweden where rodent populations are cyclic and monitoring has been running since 1971 was used. Snap-trapping was performed in approximately 60 one 1-ha plots. At each trapping, approximately 3000 traps were set during three consecutive days in September, amounting to approximately 9,000 "trap-nights".

As an index of small rodent abundance, we calculated the number of animals trapped per 100 trap nights (hereafter termed density).

The incidence of selected human diseases over time was analyzed. The national patient registry of the Swedish National Board of Health and Welfare was used. All hospitalization records between 1987 and 1996 were extracted. Two counties with complete reporting record in the northern part of the Sweden (cyclic rodents) were selected as well as one control county in the south where rodents are "non-cyclic". The International classification of diseases, $9^{th}$ revision, US Dept. Health and Human Services, PHS, Washington, D.C., 1988 number 9 (ICD 9) effective from 1987 to 1996 were used. Three conditions; gestational diabetes (diagnosis code 648A and/or 648W), severe preeclampsia (code 642F) and intrauterine fetal deaths (code 656E) were chosen on the basis of observation of the effect of Ljungan virus infection in animals. The incidence of gestational diabetes, severe preeclampsia and fetal intrauterine deaths were calculated as number of patients per 1000 full term pregnancies in that county. To increase the chances of detecting a temporal association with the rodent density in fall, admissions taking place during the second half each year (July-December) were used, as the rodent densities used were obtained in end of September each year.

Disease Concurrence in Humans

It occasionally happens that a single individual is subject to two apparently unrelated diseases. With a sufficiently large number of cases of each of the two diseases, it is possible to ask whether disease concurrence happens by chance. Utilizing the patient registry of the Swedish National Board of Health and Welfare, the concurrence frequencies of three diseases, gestational diabetes, preeclampsia and IUFD along with five control diseases [(Fracture (824), Appendicitis (640), Concussion (850), Inguinal Hernia (550), and Pneumothorax (512)] chosen on the basis of high prevalence and apparent etiological independence were examined.

Concurrence

We used the national patient registry of the Swedish National Board of Health and Welfare. All hospitalization records for all patients born 1950 to 1986 and hospitalized during the period of 1987 to 1996 were extracted. The number of records totaled 4,749,829. Disease frequencies were based on the 1987 Swedish census size of 2,036,876 females aged 0-37 years. The international disease classification (ICD) number 9 effective from 1987 to 1996 was used. Three conditions; gestational diabetes (ICD 9 diagnosis code 648A and/or 648W), severe preeclampsia (code 642F) and intrauterine fetal deaths (code 656E) were chosen on the basis of observation of the effect of Ljungan virus infection in animals (International classification of diseases, $9^{th}$ revision, US Dept. Health and Human Services, PHS, Washington, D.C., 1988). We selected five control conditions; Ankle Fracture (824), Appendicitis (640), Concussion (850), Inguinal Hernia (550), and Pneumothorax (512) not suspected to have any association with Ljungan virus infection.

Figure 2:
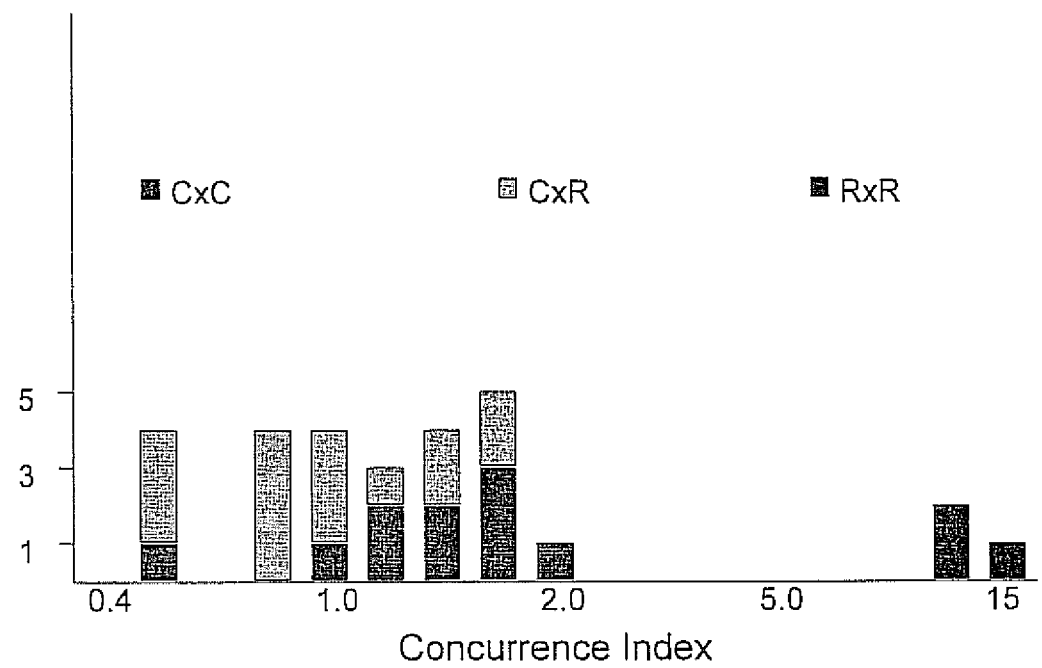
FIG. 2. Frequency distribution of disease concurrence (Ic) on a logarithmic scale for the Reproductive (R) and Control (C) disease categories, R×R, R×C, and C×C. The three reproductive diseases (with ICD9 codes) are Gestational Diabetes (648A and/or 648W), severe preeclampsia (642F) and Intrauterine Fetal Death (656E). The five Control conditions are Ankle Fracture (824), Appendicitis (640), Concussion (850), Inguinal Hernia (550), and Pneumothorax (512). The test for difference among the three disease categories is significant at P=0.004 ($X^2$=10.95, df=2; Kruskal-Wallis test).

The expected frequency of concurrence of two diseases, D1 and D2, is defined as $\text{Exp}(F_{D1D2}) = F_{D1} \times F_{D2} \times N_H$, where $F_{D1}$ and $F_{D2}$ are the overall relative frequencies of each of the two diseases and $N_H$ is the total number of individuals in the population. The index of the strength of concurrence is defined as a ratio: $I_c = \text{Obs}(F_{D1D2})/\text{Exp}(F_{D1D2})$, where Obs $(F_{D1D2})$ is the observed number of individuals having two diseases. If no excess of concurrence is present, then the ratio, Ic, is expected to be unity. Larger values of $I_c$ indicate greater excess of observed number to expected numbers of individuals (FIG. 2).

Patient Specimens

Formalin fixed paraffin embedded tissues was available from placenta tissue from 22 women with preeclampsia and 25 control women. Heart, thymus, brain and placenta from ten cases of IUFD were also examined by IHC. Frozen placenta/umbilicus samples from four preeclampsia patients and 12 healthy control patients were tested by real time RT-PCR.

Example One

Tissue Culture, Antiviral Compound

Ljungan virus was first tested in tissue culture of Vero cells in combination with Pleconaril. 1.6 micrograms of active substance per ml of the tissue culture medium were used. This dose was used in all experiment below where it says "with Pleconaril".

10 000 000 tissue culture infectious doses (TCID) of Ljungan virus treated with Pleconaril give full cytopathogenic effect (CPE) in 4 days while the control culture with no Pleconaril show full CPE in 3 days.

100 TCID of Ljungan viruses are fully inhibited if the cells were treated with Pleconaril. For a control picornavirus known not to be sensitive to Pleconaril no inhibition of any amount of the virus can be detected. 10 000 000 (TCID) of a picornavirus known to be sensitive to Pleconaril were inhibited (no CPE). This means that Ljungan virus is semi-sensitive" or "semi-resistant" to Pleconaril.

Example Two

Diabetic Bank Voles Antiviral Compound

Bank voles with diabetes were randomised into 2 groups one treated with Pleconaril and one not receiving any treatment. Treated animals were given 100 mg Pleconaril per kg body weight per day seven days. The drug was administered orally in the drinking water. All animals were subjected to a glucose tolerance test the day before the treatment and again 15 days later. Glucose tolerance test was performed by administrating 2 grams of glucose per kg BW intraperitoneally. The blood glucose levels were measured after 60 min.

In the treated group 2 out of six animals improved and had blood glucose levels decreasing more than 200 mg per dl while this was not seen in any of the six control animals.

This shows for the first time that a chronic disease, in this case diabetes, can be reversed by oral ingestion of an antiviral compound.

Example Three

Encephalitis in Arctic Fox

The arctic fox in Sweden is a species close to being extinct. The reason for this is unknown. Nordens Ark has a breeding program for arctic foxes with the aim to save the species. However, several animals in captivity have developed encephalitis and died. Nordens Ark has lost almost all their animals. The encephalitis is a slow progressing disease often starting with stereotypic behaviour followed by visual problem, loss of smell and loss of muscle coordination. The condition is slowly progressing over several months leading to the deaths of the animal. No spontaneous recovery has been seen in any of the arctic foxes observed.

Ljungan virus was isolated from the brain of one arctic fox suffering from encephalitis. Ljungan virus RNA was also detected by PCR in the brain and the heart of the same individual. Ljungan virus could also be detected in the brain and the heart by immunohistochemistry.

One arctic fox with severe encephalitis was treated with 50 mg/kg of Pleconaril twice daily for 7 days.

The clinical condition of the fox improved after the treatment in a way never seen in any of the untreated animals. However, after several months signs and symptoms of encephalitis came back. It could not be determined if this was because of re-infection or partial therapy failure.

This is the first time a chronic antiviral progressing central neural disease can be treated by an antiviral compound with significant and long lasting improvement.

Example Four

Myocarditis, Humans

Serology. Antibodies to Ljungan virus have been measured by indirect immunofluorescence tests. Four out of 5 patients with lethal myocarditis were Ljungan virus positive and only one out of 15 matched controls.

Heart tissue from patients dying from myocarditis has been tested for presence of Ljungan virus RNA by PCR in parallel with matched controls by PCR. Four out of 6 patients with myocarditis were Ljungan virus positive and none of 10 controls were found positive.

Heart tissue from patients dying from myocarditis has been tested for the presence of Ljungan virus by immunohistochemistry (IHC) in parallel with matched controls. Six out of 9 patients with myocarditis were Ljungan virus positive and one of 10 controls was found positive.

This indicates that prophylactic and/or therapeutic treatment with an antiviral compound effective against Ljungan virus of patients with myocarditis and a Ljungan virus infection will be effective against myocarditis in addition to the viral infection.

Example Five

Cardiomyopathy, Humans

Five patients with severe cardiomyopathy undergoing heart transplantation have been tested for presence of Ljungan virus in their heart by IHC. They were found to be Ljungan virus positive. This indicates that prophylactic and/or therapeutic treatment with an antiviral compound effective against Ljungan virus of patients with cardiomyopathy and a Ljungan virus infection will be effective against cardiomyopathy in addition to the viral infection.

Example Six

Type 1 Diabetes, Humans

Serology. Antibodies to Ljungan virus have been measured by indirect immunofluorescence test. 19 out of 58 (33%) patients with recent onset of type 1 diabetes were Ljungan virus positive and only 2 out of 34 (6%) of the matched controls.

Serum from patients with recent onset of type 1 diabetes has been tested for presence of Ljungan virus RNA by PCR. Two out of 30 were found positive.

Muscle tissue from patients with type 1 diabetes has been tested for presence of Ljungan virus by immunohistochemistry (IHC) in parallel with matched controls. Ten out of 12 patients with diabetes were positive and one of 10 controls were found Ljungan virus positive.

It is likely that that prophylactic and/or therapeutic treatment with an antiviral compound effective against Ljungan virus of patients with type 1 diabetes and a Ljungan virus infection will be effective against type 1 diabetes in addition to the viral infection.

Example Seven

Sudden Infant Death, Humans

Heart tissue from patients dying from sudden infant deaths (SID) has been tested for presence of Ljungan virus by immunohistochemistry. Six out of 8 patients with SID were Ljungan virus positive.

This indicates that prophylactic treatment, of the newborn or perhaps the pregnant mother, with an antiviral compound effective against Ljungan virus may reduce the risk of sudden infant death.

Example Eight

Multiple Sclerosis, Humans

Cerebrospinal fluid from patients with multiple sclerosis (MS) has been tested for presence of Ljungan virus RNA by PCR. Three out of 10 were found positive. Brain tissue from 2 patients with multiple sclerosis has been tested for presence of Ljungan virus by immunohistochemistry and both were found positive. This indicates that prophylactic and/or therapeutic treatment with an antiviral compound effective against Ljungan virus of patients with MS and a Ljungan virus infection will be effective against MS in addition to the viral infection.

Example Nine

Ljungan Virus in Laboratory Mice

LV infection, in combination with stress, resulted in a high frequency of intrauterine deaths. Infection or stress alone had little or no adverse effect on pregnancy (Table 1). Several pups, some also with severe malformations (without signs of in utero tissue degradation), predominately of the skull and brain, died in the peripartum period. Five of 8 pregnant females gave birth to a total of 12 dead pups while the group of infected and non-stressed and the group of non-infected and stressed gave birth to no dead pups and one dead pup respectively. There was a significant difference between the number of pregnant females suffering from perinatal deaths as well as between the number of offspring born dead or alive between the tree groups (see table 1). Some dead pups had no detectable pathology.

LV-infected pregnant female mice showed no signs of diabetes or abnormal glucose tolerance. However, surviving male offspring developed diabetes 10-15 weeks after birth (Table 2). Histopathology of the pancreas in all groups (I-V), using standard hematoxylin and eosin staining showed intact beta cell islets within the pancreas. Eight of 11 (73%) of the infected males had abnormal GTT results, while only 2 out of 14 (14%) of non-infected control mice had abnormal GTT (group I vs. group II, P=0.005 Fisher's exact one sided test). Infected mice also had increased abdominal fat and increased serum insulin levels (group I vs. group II P=0.008 and P<0.0001, unpaired t-test for abdominal fat and serum insulin, respectively).

Antiviral therapy using LV-specific murine antisera (group IV) or the oral antiviral compound Pleconaril (200 mg per kg body weight) administered once a day for 4 consecutive days (group III) or a combination of antiserum and Pleconaril (group V) was initiated at 5 weeks of age. The antiserum and Pleconaril treatments each reduced the frequency of animals with diabetes, as measured by GTT. In addition the combination of antiserum and Pleconaril (group V) significantly reduced serum glucose and insulin levels, as well as abdominal fat (Table 2).

TABLE 1

Outcome of pregnancy in laboratory mice subjected to Ljungan virus infection and stress

| Treatment | | | No. with Neonatal | No. of offspring born | |
|---|---|---|---|---|---|
| LV | Stress | No. of pregnant mice | deaths | Total Alive | Total Dead |
| + | 0 | 7 | 0(0%) | 67 | 0 |
| + | + | 8 | 5(63%) | 69 | 12 |
| 0 | + | 7 | 1(14%) | 81 | 1 |
| Fisher's Exact (2 × 3) test | | | p = 0.020 | | p = 0.000 |

The three treatment groups (LV infected—No stress; LV infected—with stress; Non-infected—with stress) differ in the distribution of the number of pregnant mice delivering live or stillborn pups (P=0.020). The virus alone and stress alone ups had few or no neonatal deaths, while the majority of female mice experiencing the combination of LV infection and stress had litters with neonatal deaths. Only the combination of viral infection plus stress in pregnant female mice was effective in promoting the occurrence of neonatal death.

Five treatment groups of mice, including untreated LV infected and control mice, mice treated with the antiviral compound Pleconaril, LV antisera treated, a group treated with both Pleconaril and LV antisera were examined for hyperglycemia following a standard glucose load. Overall the distribution of mice having hyperglycaemia differed among the treatments (P=0.000; Fisher's exact test). The infected, but untreated group stood apart from the other treatments with 73% of individuals hyperglycaemic. In contrast, the other treatments had low or absent incidence of hyperglycaemic mice (0-14%), and formed a statistically homogeneous subgroup (P=0.607). Each of the three treatments following LV infection was effective in reducing the frequency of hyperglycaemic response. However, only the combination therapy significantly reduced the blood glucose level at 60 min (P=0.017), the abdominal fat (P=0.012) and the serum insulin (P=0.032) concentration (using one-sided t-test comparing groups II and IV).

Disease Incidence in Humans and Rodent Density

Figure 1B:
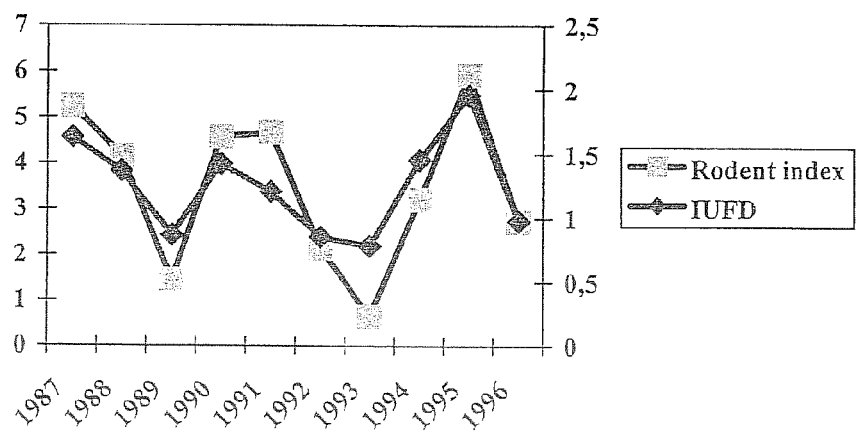
Figure 1C:
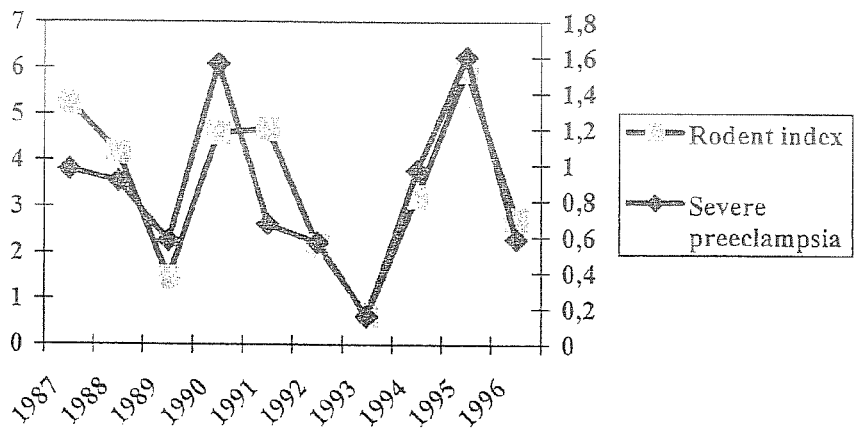

Temporal variation of incidences of both IUFD and preeclampsia were strongly associated with the cyclic rodent abundance, which had a very high coefficient of determination for both diseases of 82% and 67%, respectively (FIG. 1B and FIG. 1C). The temporal associations were direct and no time lags were seen. Also, preeclampsia and IUFD incidences covaried temporally (p=0.0012, r=0.87). Gestational diabetes occurred with a similar incidence pattern as the other diseases following peaks in small rodent abundance without any time lag, but this association did not reach statistical significance (FIG. 1A).

The southern incidences of gestational diabetes, IUFD and preeclampsia with those in the north were compared. This comparison did not reveal any strong or significant correspondence of disease incidences in the north and south. Furthermore, none of the three diseases in the south was significantly correlated with rodent densities in the north. These tests show that fluctuations in disease incidence in the north do not occur nationwide, and, as expected, rodent cycling in the north is not influencing disease incidence in the south, where rodents do not cycle.

Concurrence

The three reproductive and five control diseases were examined in all pair-wise tests for disease concurrence. We define the concurrence index (Ic) as the ratio between observed concurrence of two diseases and the expected concurrence (see online material for IC definition and Ic data). The ten concurrence indices among the five control diseases (C×C) had a mean Ic of 1.4. A Similar pattern was present for the 15 pair-wise concurrences between the reproductive diseases and the five control diseases (R×C), in which the mean Ic was 1.0. In contrast, the three pair wise Ic values for gestational diabetes, preeclampsia and IUFD (R×R) had a mean value of 12.7, which is significantly different from the other two groups (FIG. 2). This evidence is consistent with the hypothesis that a single causative agent underlies gestational diabetes, preeclampsia and IUFD.

Because diabetes is associated with a number of diseases, often manifesting some time after the onset of the diabetes, we tested the hypothesis that preeclampsia and IUFD may be natural, albeit unusual, sequelae of gestational diabetes by examining the order of onset for all cases of concurrent disease among the three conditions. The disease of first onset could be either preeclampsia and IUFD or gestational diabetes. This supports the supposition that both preeclampsia and IUFD are causally independent of gestational diabetes, and that the three diseases can be the independent outcome of a common factor.

Patient Specimens

Figure 3:
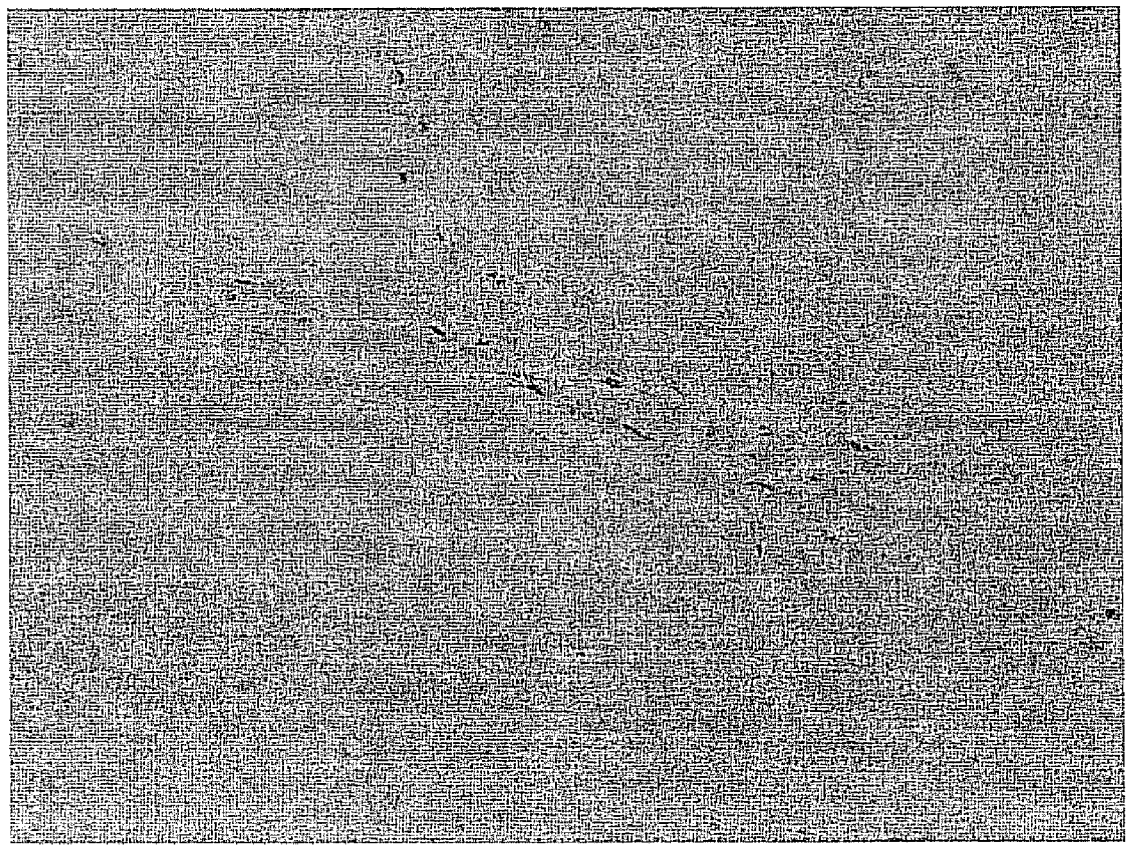
FIG. 3. Vascular staining of Ljungan virus antigen (red) of formalin fixed brain tissue from case with intrauterine fetal deaths using immunohistochemistry.
Figure 4:
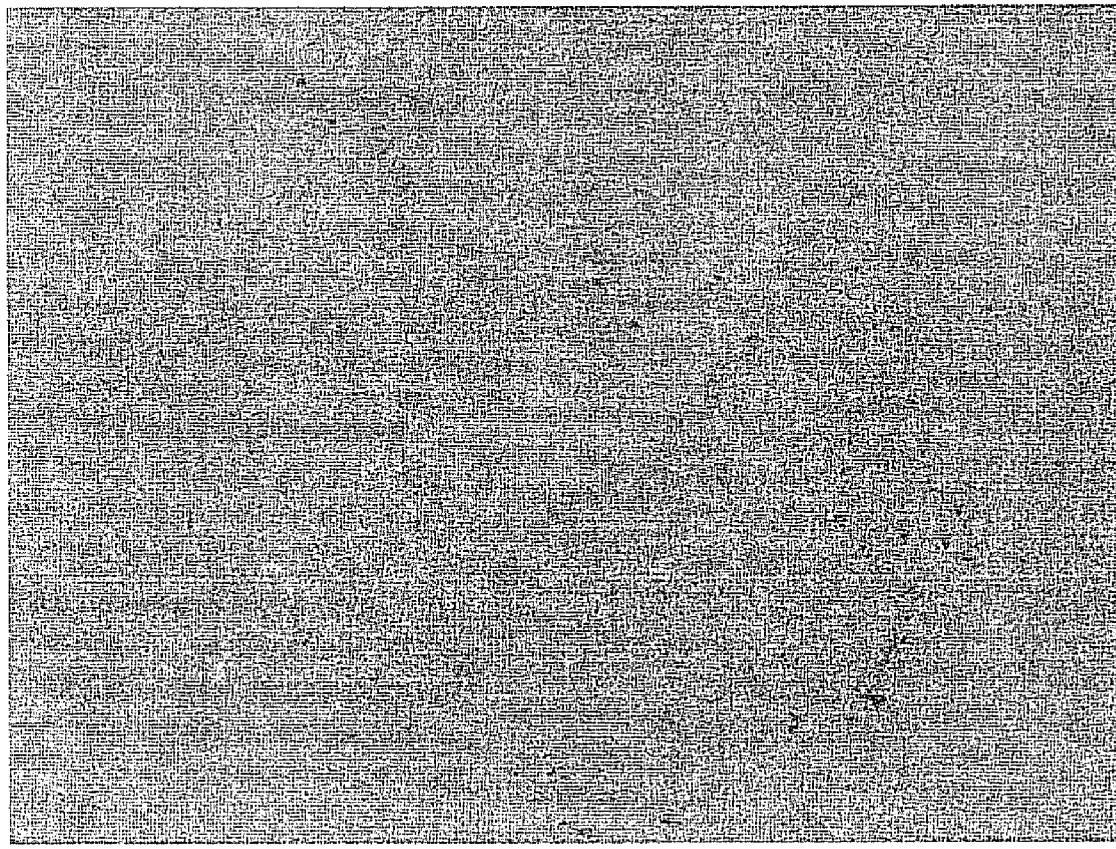
FIG. 4. Vascular staining of Ljungan virus antigen (red) in placenta tissue in a patient with preeclampsia.
Figure 5:
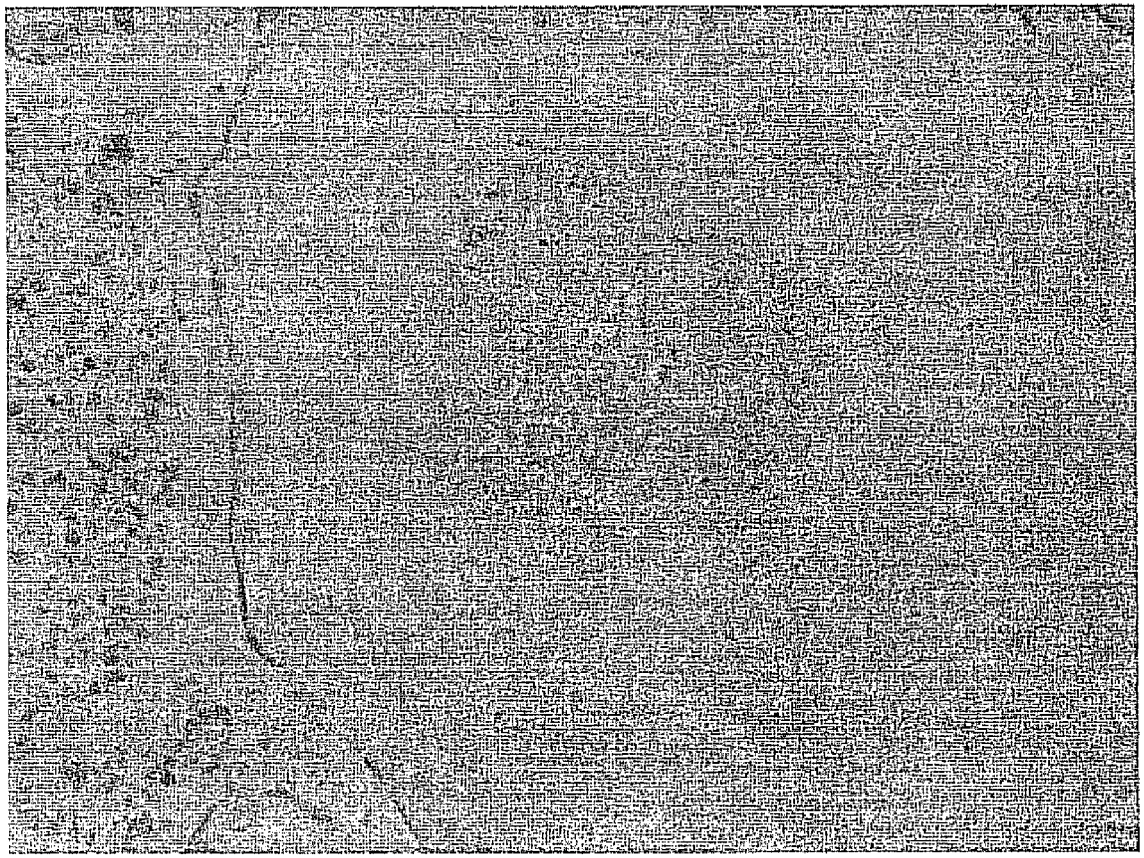
FIG. 5. Vascular staining of Ljungan virus antigen (red) in placenta tissue in a patient with preeclampsia.

In the group of women with preeclampsia, 12 of the placentas tested positive and 10 tested negative by the IHC assay, whereas all 25 of the control placental samples tested negative (P<0.0001; Fisher's exact test). Using the same IHC, formalin-fixed tissue samples of heart, thymus, brain and placenta from ten cases of IUFD were examined. Two of the cases were positive for LV in several of the organs examined. Endothelial and peri-vascular staining of the brain from a case of IUFD is shown in FIG. 3. The pattern of staining blood vessels was noted in many different organs, including pancreas, placenta and brain in the human samples and in all of the rodent species tested.

LV is difficult to cultivate in tissue culture, making isolation of virus an inefficient diagnostic approach. A real time RT-PCR for quantitative measurement of LV RNA has therefore been developed (Donoso-Mantke O, Niklasson B, Kallies R, Nitsche A Meyer R and Niedrig M. First quantitative real-time reverse transcriptase PCR assay for detection of Ljungan virus manuscript submitted). Using this assay, placenta/umbilicus samples from two out of four preeclampsia patients tested positive while all 12 healthy control patients were PCR-negative. Each of the positive specimens contained 10-50 copies of LV RNA and for each of these the PCR product was verified by sequence analysis. Mice infected shortly after birth and sacrificed one week after LV infection and onset of severe encephalitis were PCR positive with one thousand to a million RNA copies per gram tissue (see online material). In contrast mice infected shortly after birth and sacrificed 15 weeks later at the onset of diabetes tested negative for LV, with the exception of barely detectable levels of LV RNA found in pancreatic samples from some of the animals. Low LV RNA copy numbers were also found in 6 placenta specimens from infected pregnant female mice. No association between the number of RNA copies detected and the clinical outcome was found in LV-infected pregnant mice.

Discussion

An infectious aetiology has long been suggested for T1D, and several viral agents have been proposed based on either observations of virus associated with disease in humans or the fact that virus can induce diabetes in laboratory animals. Rubella virus, cytomegalovirus, varicella zoster and cardio virus have been implicated (20-22). Most attention has been directed at Coxsackie B viruses, where the virus has been recovered from pancreas of patients with recent onset of diabetes (23-24). Coxsackie B virus can also induce diabetes in some strains of laboratory mice using specific strains of virus (25). However, epidemiological and clinical studies attribute only a very small fraction of human diabetes cases to any of these agents.

In contrast, Ljungan virus can be responsible for a substantial fraction of cases of diabetes, as well as preeclampsia and IUFD. This is based on an assessment of the complete range of evidence generated and summarized in Table 3. The fact that disease found in wildlife and associated with LV can be transmitted in laboratory animals and thus fulfilling Koch's postulates under controlled conditions is one component of the evidence. Previous and current studies also demonstrate an epidemiological link between the suspected reservoir and vector and human disease incidences, the unique concurrences of the human diseases involved, laboratory evidence of LV from patients, and case control studies pointing to LV in diabetes and preeclampsia.

Epidemiological studies have previously found pair wise associations between diabetes, preeclampsia and IUFD. However, the temporal associations between preeclampsia and IUFD (FIG. 1) and between the two diseases and an environmental factor (vole abundance) are described here.

For diabetes, there are pertinent observations from the animal data, which might be applicable to the human context. Gestational diabetes, T1D and T2D are different phenotypes with one common etiology. The animal data presented suggests that LV can induce both T1D and T2D symptoms depending on the species and the phase of disease within a single species. T2D, with its failing glucose regulation, high insulin output, body fat accumulation and insulin resistance, could be the first stage of the diabetes, and in which T1D, with its loss of insulin production capacity is the end stage of a single pathogenic course. In humans, T2D becomes clinically apparent when disease progression is slow, as is typically true for older individuals. By this view T1D is the final stage that rapidly reaches clinical expression in young people with a mean incubation time according to our previous studies of only two years. The lighter and typically temporary manifestation of gestational diabetes with its abnormal glucose tolerance becoming apparent shortly after infection can be part of the same underlying pathology, perhaps precipitated by the diabetogenic stress of pregnancy.

Ljungan virus creates a persistent non-cytopathogenic infection in a wide variety of tissue cultures and the available evidence proves that it causes a long lasting or chronic infection in laboratory mice developing late onset disease. Additionally, the association with stress and the course of Ljungan virus infection, as shown here, is concordant with many clinical observations on stress and diabetes in humans.

LV causes a wide variety of diseases in the individuals affected and can also infect and cause disease in many different species. Available laboratory data prove that the diabetes mouse model is not restricted to CD1 mice or any specific isolate of Ljungan virus (Niklasson unpublished). A wide host range of Ljungan virus, including several species of native rodents and the arctic fox, and several Ljungan virus isolates have also been found from wild rodents of North America. The presence of LV on two continents in various species and the recent suggestion that LV and the related parechoviruses can be close to the root in the picornavirus family based on phylogenetic analysis suggest that this virus can be widely distributed.

The pathogenesis of Ljungan virus remains to be investigated. Long lasting or chronic infection, in which preliminary immunohistochemical observations suggest vascular tropism, can be important, especially since LV seems to infect many different organs including muscle, glands and brain. Experiments on LV treatment in a mouse diabetes model (Table 2) showed that both Ljungan virus antisera and an antiviral agent were useful in addressing the primary underlying diabetes effects. The possibility of halting viral replication opens up possible studies on the role of the immune system and the question of autoimmunity in contrast to an adequate immune response to viral invasion. The potential utility of antisera and antiviral treatment suggests new therapeutic avenues for diseases which can be due to LV infection.

The assays used to detect the presence of LV or LV immunity is based on recently developed diagnostic tools. Validation of these tools often takes advantage of established standards as controls. In the case of a novel virus this is initially very difficult. In spite of this, the human data presented using a combination of assays prove that Ljungan virus infects humans. In addition, the findings, although based on limited numbers and a somewhat scattered collection of specimens, show a consistent link with all three diseases, suggesting direct LV causation. Furthermore the laboratory results are in line with expectations from the animal models, including variations in viral titers over the course of a disease.

The epidemiology, the supporting animal data and the human laboratory results each point to the likelihood of a single specific infectious etiology for three diseases which are all of significant importance for human morbidity and mortality.

Example Ten

As a control, gestational diabetes, IUFD and preeclampsia patients in the cyclic rodent region were compared to patients in the south of Sweden (Skåne county), where the rodent population is non-cyclic. Associations were absent between patients in the north vs. patients in the south and also between rodent density in the north and patients in the south. The significance of the slope of the regression coefficient was used to test for association. No significant autocorrelation in the residuals were present.

TABLE 3

Comparison of disease and rodent density in the north and south of Sweden

| | |
|---|---|
| IUFD in the south vs. IUFD in the north | $P = 0.221$ |
| IUFD in the south vs. rodents in the north | $P = 0.153$ |
| Severe preeclampsia in the south vs. severe preeclampsia in the north | $P = 0.470$ |
| Severe preeclampsia in the south vs. rodents in the north | $P = 0.267$ |
| Gestational diabetes in the south vs. gestational diabetes in the north | $P = 0.080$ |
| Gestational diabetes in the south vs. rodents in the north | $P = 0.139$ |

The number of patients per 1000 term pregnancies with gestational diabetes (ICD9 648A and/or 648W) and intrauterine fetal deaths (ICD9 656E) over the time period 1987-

1996 per 1000 delivery were also calculated for the county of Gotland (vole free island) and for the study region in the north (Gävleborgs and Västernorrlands county) as well as the entire mainland (all of Sweden except Gotland).

TABLE 4

|  | IUFD index | Chi square one sided | Gestational diabetes index | Chi square one sided |
|---|---|---|---|---|
| Gotland | 1.59 |  | 1.71 |  |
| Study area in north (cyclic voles) | 3.02 | p = 0.01 | 2.68 | p = 0.06 |
| Entire Sweden except Gotland | 2.68 | p = 0.03 | 2.87 | p = 0.03 |

TABLE 5

The absolute number of cases recorded (total number) of the different diseases tested pair wise, and the concurrence index for each pair of diseases.

|  | Total number | Gestational Diabetes | Severe preecl | IUFD | Pneumothorax | Inguinal hernia | App | Fract ankle |
|---|---|---|---|---|---|---|---|---|
| Gestational diabetes | 3550 |  |  |  |  |  |  |  |
| Severe preeclampsia | 2214 | 12.4 |  |  |  |  |  |  |
| IUFD | 3333 | 15.1 | 10.5 |  |  |  |  |  |
| Pneumothorax | 1348 | 0.4 | 0.7 | 1.8 |  |  |  |  |
| Inguinal hernia | 3169 | 0.7 | 1.5 | 1.0 | 1.4 |  |  |  |
| Appendicitis | 32729 | 1.4 | 0.9 | 0.7 | 0.5 | 1.3 |  |  |
| Fractured ankle | 8543 | 1.7 | 0.9 | 1.1 | 1.8 | 1.0 | 1.0 |  |
| Concussion | 31220 | 1.0 | 0.6 | 0.5 | 1.6 | 1.5 | 1.7 | 2.2 |

Mouse RT-PCR Data

Mice infected during the first days of life and sacrificed one week later at the time of clinical symptoms of severe encephalitis. Organ were frozen at −70° C., shipped on dry ice and analysed by a real time RT-PCR for quantitative measurement of LV RNA (Donoso-Mantke O, Niklasson B, Kallies R, Nitsche A Meyer R and Niedrig M. First quantitative real-time reverse transcriptase PCR assay for detection of Ljungan virus manuscript submitted). The results (Table 6) are given as number of RNA copies per gram tissue.

TABLE 6

RT-PCR measure of LV RNA in infected mice.

| Mouse ID number and organ | PCR result | RNA copy Number |
|---|---|---|
| 1 CNS | positive | $3.8 * 10^5$ |
| 2 CNS | positive | $1 * 10^7$ |
| 3 CNS | positive | $8.9 * 10^6$ |
| 4 CNS | positive | $7.6 * 10^6$ |
| 5 CNS | positive | $4 * 10^4$ |
| 6 CNS | positive | $5.5 * 10^6$ |
| 1 liver | positive | $1 * 10^4$ |
| 2 liver | positive | $2 * 10^4$ |
| 3 liver | positive | $9 * 10^3$ |
| 4 liver | positive | $9 * 10^3$ |
| 5 liver | positive | 10 |
| 6 liver | positive | $6 * 10^3$ |
| 1 lung | positive | $2 * 10^4$ |
| 2 lung | positive | $3 * 10^3$ |
| 3 lung | positive | $1 * 10^3$ |
| 4 lung | positive | $5 * 10^2$ |
| 5 lung | negative | — |
| 6 lung | positive | $7 * 10^3$ |
| 1 kidney | positive | $4 * 10^3$ |
| 2 kidney | positive | $4 * 10^3$ |
| 3 kidney | positive | $8 * 10^2$ |
| 4 kidney | positive | $6 * 10^2$ |
| 5 kidney | positive | 1 |
| 6 kidney | Negative | — |
| 1 pancreas | Positive | $3.9 * 10^4$ |
| 2 pancreas | Positive | $1.6 * 10^4$ |
| 3 pancreas | Positive | $1.1 * 10^4$ |
| 4 pancreas | Positive | $2 * 10^2$ |
| 5 pancreas | Indeterminate | — |
| 6 pancreas | Positive | $3 * 10^2$ |
| 1 heart | Positive | $1.6 * 10^4$ |
| 2 heart | Positive | $1.5 * 10^4$ |
| 3 heart | Positive | $8 * 10^3$ |
| 4 heart | Positive | $2.5 * 10^4$ |
| 5 heart | Positive | $1.1 * 10^4$ |
| 6 heart | Positive | $1.4 * 10^5$ |

Example Eleven

Mice were treated with a combination of Pleconaril and antisera and interferon α. Interferon α was given as 2×10⁷ IU/kg/day during three consecutive days during the same week Pleconaril and specific immunoglobulin was administrated. As a result, this example proves that the combination therapy of Pleconaril, antisera, and interferon reduced the frequency of diabetes as defined by a pathological glucose tolerance test as did Pleconaril alone, antisera alone, and the combination of antisera and Pleconaril. In addition, the combination therapy (Pleconaril, antisera, and interferon) normalize the amount of abdominal fat and the level of serum insulin, reducing them to normal levels. Table 7 below demonstrates the above conclusions.

TABLE 7

| Group | No. Mice | No. Hyperglycemic | Blood glucose (mg/dL) @ 60 minutes | Abdominal fat (g) | Serum insulin (µg/L) |
|---|---|---|---|---|---|
| Non-infected Controls | 10 | 2 (20%) | 196 (25) | 1.76 (0.58) | 1.09 (1.03) |
| Infected: No treatment | 11 | 8 (73%) | 242 (75) | 2.90 (0.84) | 5.04 (2.30) |
| Infected: Pleconaril | 11 | 1 (9%) | 211 (79) | 2.20 (1.0) | 4.15 (5.03) |
| Infected: Antisera | 10 | 0 (0%) | 210 (73) | 2.51 (1.1) | 6.67 (6.80) |
| Infected: Pleconaril + Antisera | 10 | 0 (0%) | 181 (39) | 2.08 (0.66) | 2.87 (2.60) |
| Infected: Pleconaril + Antisera + Interferon | 12 | 0 (0%) | 179 (43) | 1.87 (0.61) | 1.5 (1.55) |

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

Lee, H. W., Lee, P. W. & Johnson, K. M. (1978) Isolation of the etiologic agent of Korean Hemorrhagic fever, *J. Infect. Dis.* 137 3): 298-308.

Niklasson, B. & LeDuc, J. (1984) Isolation of the nephropathia epidemica agent in Sweden. *Lancet* May 5; 1: 1012-3.

Nichol, S. T., Spiropoulou, C. F., Morzunov, S., Rollin, P. E., Ksiazek, T. G., Feldmann, H., Sanchez, A., Childs, J., Zaki, S & Peters C. J. (1993) Genetic identification of a hantavirus associated with an outbreak of acute respiratory illness. *Science*, 262, 914-7.

Niklasson, B., Hörnfeldt, B & Lundman, B. (1998) Could myocarditis, insulin-dependent diabetes mellitus, and Guillain-Barré syndrome be caused by one or more infectious agents carried by rodents? *Emerging Infectious Diseases* 4 (2):187-93.

Niklasson, B., Kinnunen, L., Hörnfeldt, B., Hörling, J., Benemar, C., Hedlund, K. O., Matskova, L., Hyypia, T & Winberg G. (1999) A new picornavirus isolated from bank voles (Clethrionomys glareolus). *Virology* 255(1):86-93.

Johansson, S., Niklasson, B., Maizel, J., Gorbalenya, A. E & Lindberg A M. (2002) Molecular analysis of three Ljungan virus isolates reveals a new, close-to-root lineage of the Picornaviridae with a cluster of two unrelated 2A proteins. *J. Virol.* 76 (17):8920-30.

Schoenecker, B., Heller, K. E & Freimanis, T. (2000). Development of stereotypes and polydipsia in wild caught bank voles (Clethrionomys glareolus) and their laboratory-bred offspring. Is polydipsia a symptom of diabetes mellitus? *Applied Animal Behaviour Science* 68 (4):349.

Niklasson, B., Heller, K. E., Schonecker, B., Bildsoe, M., Daniels, T., Hampe, C. S., Widlund, P., Simonson, W. T., Schaefer, J. B., Rutledge E, et al. (2003) Development of type 1 diabetes in wild bank voles associated with islet autoantibodies and the novel Ljungan virus. *Int. J. Exp. Diabesity Res.* 4 (1):35-44.

Niklasson, B., Hornfeldt, B., Nyholm, E., Niedrig, M., Donoso-Mantke, O., Gelderblom, H. R & Lernmark A. (2003) Type 1 diabetes in Swedish bank voles (Clethrionomys glareolus): signs of disease in both colonized and wild cyclic populations at peak density. *Ann. N Y. Acad. Sci.* 1005:170-5.

Freimanis, T., Heller, K. E., Schoenecker, B., Bildsoe, M. (2003) Effects of postnatal stress on the development of type 1 diabetes in bank voles (Clethrionomys glareolus). *Int. J. Exp. Diabesity Res.* 4(1):21-5.

Florea, N. R., Maglio, D & Nicolau, D. P. (2003) Pleconaril, a novel antipicornaviral agent. *Pharmacotherapy* 23(3): 339-48.

Romero, J. R. (2001) Pleconaril: a novel antipicornaviral drug. *Expert Opinion on Investigational Drugs* 10(2):369-79.

Pevear, D. C., Tull, T. M., Seipel, M. E., Groarke, J. M, (1999) Activity of pleconaril against enteroviruses. *Antimicrob. Agents Chemother.* 43(9):2109-15.

O'Sullivan, J. B. (1991) Diabetes mellitus after GDM. *Diabetes.* December; 40 Suppl 2: 131-5.

Suhonen, L & Teramo K. (1993) Hypertension and pre-eclampsia in women with gestational glucose intolerance *Acta Obstet. Gynecol. Scand.* May; 72(4): 269-72.

Hansson, L & Henttonen H. (1985) Gradients in density variations of small rodents: the importance of latitude and snow cover. *Oecologia* 67:394-402.

Hansson, L & Henttonen, H. (1988). Rodent dynamics as community process. *Trends Ecol. Evol.* 3, 195-200.

Hörnfeldt, B. (1994) Delayed density dependence as a determinant of vole cycles. *Ecology.* 75: 791-806.

Hörnfeldt, B. (2004) Long-term decline in numbers of cyclic voles in boreal Sweden: analysis and presentation of hypothesis. *Oikos* 107, 376-392.

Nicoletti, F., Scalia, G., Lunetta, M., Condorelli, F., Di-Mauro, M., Barcellini, W. M, Stracuzzi, S., Pagano, M & Meroni, P. L. (1990) Correlation between islet cell antibodies and anti-cytomegalovirus IgM and IgG antibodies in healthy first-degree relatives of type 1 (insulin-dependent) diabetic patients. *Clin. Immunol. Immunopathol.* April; 55(1): 139-47.

Ginsberg-Fellner, F., Witt, M. E., Yagihashi, S., Dobersen, M. J., Taub, F., Fedun, B., McEvoy, R. C., Roman, S. H., Davies, R. G., Cooper L Z, et-al (1984) Congenital rubella syndrome as a model for type 1 (insulin-dependent) diabetes mellitus: increased prevalence of islet cell surface antibodies. *Diabetologia.* July; 27 Suppl: 87-9.

Champsaur, H. F., Bottazzo, G. F., Bertrams, J., Assan, R & Bach, C. (1982) Virologic, immunologic, and genetic factors in insulin-dependent diabetes mellitus. *J. Pediatr.* January; 100 (1): 15-20.

Yoon, J. W., Austin, M., Onodera, T & Notkins, A. L. (1979) Isolation of a virus from the pancreas of a child with diabetic ketoacidosis. *New. Engl. J. Med.* May 24; 300(21): 1173-9.

Notkins, A. L., Yoon, J., Onodera, T & Jenson, A. B. (1979) Virus-induced diabetes mellitus: infection of mice with variants of encephalomyocarditis virus, coxsackievirus B4, and reovirus type 3. *Adv. Exp. Med. Biol.* 119: 137-46.

Webb, S. R., Loria, R. M., Madge, G. E & Kibrick, S. (1976) Susceptibility of mice to group B coxsackie virus is influenced by the diabetic gene. *J. Exp. Med.* May 1; 143(5): 1239-48.

Nilsson, A. C., Spetz, C. L., Carsjö, K., Nightingale, R. & Smedby, B. (1994) Reliability of the hospital registry. The diagnostic data are better than their reputation. *Läkartidningen* 91, 598 603-598 605.

Sonderegger-Iseli, K., Burger, S., Muntwyler, J. & Salomon, F. (2000) *Lancet* 355, 2027-2031.

Zhu, L., Nakabayashi, M & Takeda Y. (1997) Statistical analysis of perinatal outcomes in pregnancy complicated with diabetes mellitus. *J. Obstet. Gynaecol. Res.* December; 23(6): 555-63.

Murphy, D. J & Stirrat, G. M. (2000) Mortality and morbidity associated with early-onset preeclampsia. *Hypertens. Pregnancy.* 19(2): 221-31.

Aberg, A., Rydhstrom, H., Kallen, B & Kallen, K. (1997) Impaired glucose tolerance during pregnancy is associated with increased fetal mortality in preceding sibs. *Acta Obstet Gynecol. Scand.* March; 76(3): 212-7.

Girz, B. A., Divon, M. Y & Merkatz, I. R (1992) Sudden fetal death in women with well-controlled, intensively monitored gestational diabetes, *J. Perinatol.* September; 12(3): 229-33

Williams, D. (2003) Pregnancy: a stress test for life. *Curr. Opin. Obstet. Gynecol.* December; 15(6): 465-71.

Sepa, A., Wahlberg, J., Vaarala, O., Frodi, A & Ludvigsson, J. (2005) Psychological stress may induce diabetes-related autoimmunity in infancy. *Diabetes Care.* February; 28(2): 290-5.

Wales, J. K, (1995) Does psychological stress cause diabetes? *Diabet. Med.* February; 12(2): 109-12.

Vialettes, B., Ozanon, J. P., Kaplansky, S., Farnarier, C., Sauvaget, E., Lassmann-Vague, V., Bernard, D & Vague, P. (1989) Stress antecedents and immune status in recently diagnosed type I (insulindependent) diabetes mellitus. *Diabet. Metab.* January-February; 15(1): 45-50.

Main, A. J., Shope, R. E & Wallis, R. C. (1976) Characterization of Whitney's Clethrionomys gapperi virus isolates from Massachusetts. *J. Wildl. Dis.* April 12 (2) 154-64.

Whitney, E., Roz, A. P & Rayner, G. A. (1970) Two virus isolated from rodents (Clethrionomys gapperi and Microtus pennsylvanicus) trapped in St Lawrence County, New York. *J. Wildl. Dis.* Vol 6, 48-55.

Hughes, A. L (2004) Phylogeny of the Picornaviridae and differential evolutionary divergence of picornavirus proteins. *Infect. Genet Evol.* June; 4(2): 143-52.

Johansson, S., Niklasson, B., Maizel, J., Gorbalenya, A. E & Lindberg, A. M. (2002) Molecular analysis of three Ljungan virus isolates reveals a new, close-to-root lineage of the Picornaviridae with a cluster of two unrelated 2A proteins. *J. Virol.* September; 76(17): 8920-30.

What is claimed is:

1. A method of therapeutic treatment of Amyotrophic Lateral Sclerosis (ALS) in a mammal infected with Ljungan virus, comprising administrating to said mammal an antivirally effective amount of pleconaril.

2. The method according to claim 1, wherein the mammal is selected from the group consisting of humans, horses, cattle, pigs, cats, dogs and rodents.

3. The method according to claim 1, wherein the Ljungan virus infection is in neural cells of the mammal.

4. The method according to claim 3, wherein the neural cells are brain cells.

5. A method of treatment of Amyotrophic Lateral Sclerosis (ALS) in a mammal infected with Ljungan virus, comprising the step of administering to the mammal an antivirally effective amount of a composition comprising pleconaril, antiserum including anti-Ljungan virus antibodies, and an interferon.

6. The method according to claim 1, wherein said administering step further includes administering an anti-Ljungan virus antibody.

7. The method according to claim 1, wherein said administering step further includes administering an interferon.

* * * * *